(12) United States Patent
Harjunmaa et al.

(10) Patent No.: US 8,175,666 B2
(45) Date of Patent: May 8, 2012

(54) THREE DIODE OPTICAL BRIDGE SYSTEM

(75) Inventors: Hannu Harjunmaa, Holden, MA (US);
Stevan Kun, Worcester, MA (US);
Rebecca Burrell, Rowley, MA (US);
Georg Leuenberger, Hofstetten (CH)

(73) Assignee: Grove Instruments, Inc., Worcester, MA (US)

( * ) Notice: Subject to any disclaimer, the term of this patent is extended or adjusted under 35 U.S.C. 154(b) by 1536 days.

(21) Appl. No.: 11/526,564

(22) Filed: Sep. 25, 2006

(65) Prior Publication Data
US 2007/0208238 A1    Sep. 6, 2007

Related U.S. Application Data

(63) Continuation-in-part of application No. 11/335,833, filed on Jan. 19, 2006, now abandoned, which is a continuation of application No. 10/134,310, filed on Apr. 26, 2002, now Pat. No. 7,003,337.

(51) Int. Cl.
*A61B 5/1455* (2006.01)
(52) U.S. Cl. ......................... 600/316; 600/310
(58) Field of Classification Search .......... 600/300–344; 422/68.1–82.13; 250/330–334
See application file for complete search history.

(56) References Cited

U.S. PATENT DOCUMENTS

| | | | |
|---|---|---|---|
| 1,758,088 A | 5/1930 | Schmick | |
| 2,721,942 A | 10/1955 | Friel et al. | |
| 3,463,142 A | 8/1969 | Harte | |
| 3,489,906 A | 1/1970 | Beer | |
| 3,614,450 A | 10/1971 | Hill et al. | |
| 3,638,640 A | 2/1972 | Shaw | |
| 3,799,672 A | 3/1974 | Vurek | |
| 3,926,527 A | 12/1975 | Pembrook et al. | |
| 3,957,037 A | 5/1976 | Fletcher et al. | |

(Continued)

FOREIGN PATENT DOCUMENTS

EP    0 074 428 B1    3/1983

(Continued)

OTHER PUBLICATIONS

Spanner, G., et al., "New Concept for the Non-Invasive Determination of Physiological Glucose Concentrations Using Modulated Laser Diodes", *Fresenius J. Anal. Chem* (1996) 354: 306-310.

(Continued)

*Primary Examiner* — Eric Winakur
*Assistant Examiner* — Marjan Fardanesh
(74) *Attorney, Agent, or Firm* — Hamilton, Brook, Smith & Reynolds, P.C.

(57) ABSTRACT

An improved method for non-invasively measuring a concentration of a target analyte dissolved in a fluid flowing through a sample is presented. It includes directing a probe beam of electromagnetic radiation, having time multiplexed components of different wavelengths, where at least one of the time-multiplexed components consists of two different simultaneous wavelengths through the sample and measuring the difference of the absorption of the radiation of the time-multiplexed components at different sample states. During sample state changes, the amount of fluid containing the target analyte within the sample is changing, varying the total amount of target analyte in the sample, and the absorption properties of the sample. The sample states may be produced by compressing and uncompressing the tissue sample. The method is useful in measuring the concentration of a target analyte, such as glucose, in tissue containing blood.

6 Claims, 1 Drawing Sheet

U.S. PATENT DOCUMENTS

| | | | |
|---|---|---|---|
| 3,958,560 | A | 5/1976 | March |
| 3,963,019 | A | 6/1976 | Quandt |
| 4,029,085 | A | 6/1977 | DeWitt et al. |
| 4,033,330 | A | 7/1977 | Willis et al. |
| 4,169,676 | A | 10/1979 | Kaiser |
| 4,266,554 | A | 5/1981 | Hamaguri |
| 4,267,844 | A | 5/1981 | Yamanishi |
| 4,306,877 | A | 12/1981 | Lübbers |
| 4,321,930 | A | 3/1982 | Jöbsis et al. |
| 4,380,240 | A | 4/1983 | Jöbsis et al. |
| 4,398,541 | A | 8/1983 | Pugliese |
| 4,427,889 | A | 1/1984 | Müller |
| 4,447,150 | A | 5/1984 | Heinemann |
| 4,485,820 | A | 12/1984 | Flower |
| 4,490,845 | A | 12/1984 | Steinbruegge et al. |
| 4,513,751 | A | 4/1985 | Abe et al. |
| 4,523,279 | A | 6/1985 | Sperinde et al. |
| 4,570,638 | A | 2/1986 | Stoddart et al. |
| 4,586,513 | A | 5/1986 | Hamaguri |
| 4,603,700 | A | 8/1986 | Nichols et al. |
| 4,621,643 | A | 11/1986 | New, Jr. et al. |
| 4,641,658 | A | 2/1987 | Lepper |
| 4,653,498 | A | 3/1987 | New, Jr. et al. |
| 4,655,225 | A | 4/1987 | Dähne et al. |
| 4,694,833 | A | 9/1987 | Hamaguri |
| 4,704,029 | A | 11/1987 | Van Heuvelen |
| 4,714,080 | A | 12/1987 | Edgar, Jr. et al. |
| 4,725,147 | A | 2/1988 | Stoddart |
| 4,750,496 | A | 6/1988 | Reinhart et al. |
| 4,759,369 | A | 7/1988 | Taylor |
| 4,768,516 | A | 9/1988 | Stoddart et al. |
| 4,785,814 | A | 11/1988 | Kane |
| 4,796,636 | A | 1/1989 | Branstetter et al. |
| 4,805,623 | A | 2/1989 | Jöbsis |
| 4,817,623 | A | 4/1989 | Stoddart et al. |
| 4,819,752 | A * | 4/1989 | Zelin ............ 600/322 |
| 4,832,484 | A | 5/1989 | Aoyagi et al. |
| 4,854,699 | A | 8/1989 | Edgar, Jr. |
| 4,863,265 | A | 9/1989 | Flower et al. |
| 4,867,557 | A | 9/1989 | Takatani et al. |
| 4,882,492 | A | 11/1989 | Schlager |
| 4,883,055 | A | 11/1989 | Merrick |
| 4,907,594 | A | 3/1990 | Muz |
| 4,927,264 | A | 5/1990 | Shiga et al. |
| 4,975,581 | A | 12/1990 | Robinson et al. |
| 5,028,787 | A | 7/1991 | Rosenthal et al. |
| 5,054,487 | A | 10/1991 | Clarke |
| 5,099,123 | A | 3/1992 | Harjunmaa |
| 5,112,124 | A | 5/1992 | Harjunmaa et al. |
| 5,137,023 | A | 8/1992 | Mendelson et al. |
| 5,167,230 | A | 12/1992 | Chance |
| 5,178,142 | A * | 1/1993 | Harjunmaa et al. ........ 600/310 |
| 5,183,042 | A | 2/1993 | Harjunmaa et al. |
| 5,190,040 | A | 3/1993 | Aoyagi |
| 5,267,152 | A | 11/1993 | Yang et al. |
| 5,277,181 | A | 1/1994 | Mendelson et al. |
| 5,322,067 | A | 6/1994 | Prater et al. |
| 5,348,002 | A * | 9/1994 | Caro ............ 600/310 |
| 5,372,135 | A | 12/1994 | Mendelson et al. |
| 5,620,000 | A | 4/1997 | Zinser et al. |
| 5,746,206 | A | 5/1998 | Mannheimer |
| 5,827,181 | A | 10/1998 | Dias et al. |
| 6,151,516 | A * | 11/2000 | Kiani-Azarbayjany et al. ............ 600/322 |
| 6,223,063 | B1 | 4/2001 | Chaiken et al. |
| 6,285,894 | B1 | 9/2001 | Oppelt et al. |
| 6,292,686 | B1 | 9/2001 | Chaiken et al. |
| 6,400,972 | B1 | 6/2002 | Fine |
| 6,615,061 | B1 | 9/2003 | Khalil et al. |
| 2003/0204133 | A1 | 10/2003 | Harjunmaa et al. |
| 2004/0173737 | A1 | 9/2004 | Shimomura et al. |

FOREIGN PATENT DOCUMENTS

| | | |
|---|---|---|
| EP | 0 152 979 A1 | 8/1985 |
| EP | 0 226 822 A2 | 7/1987 |
| EP | 0 160 768 B1 | 5/1989 |
| EP | 0 404 562 B1 | 12/1990 |
| EP | 0 407 992 A1 | 1/1991 |
| EP | 0 997 103 A1 | 5/2000 |
| EP | 1 189 074 A2 | 3/2002 |
| WO | WO 90/04353 | 5/1990 |
| WO | WO 90/07905 | 7/1990 |
| WO | WO 91/15991 | 10/1991 |
| WO | WO 92/17765 | 10/1992 |
| WO | WO 93/00855 | 1/1993 |
| WO | WO 98/43096 | 10/1998 |

OTHER PUBLICATIONS

Peura, R.A., et al., "Blood Glucose Sensors: An Overview", *IEEE/NSF Symposium on Biosensors*, 1984, pp. 63-68.

Heise, H.M., et al., "Multivariate Determination of Glucose in Whole Blood by Attenuated Total Reflection Infrared Spectroscopy", *Anal. Chem.* 1989, 61, 2009-2015.

Arnold, M., et al., "Determination of Physiological Levels of Glucose in an Aqueous Matrix with Digitally Filtered Fourier Transform Near-Infrared Spectra", *Anal. Chem.* 1990, 62, 1457-1464.

Marbach, R., et al., "Calibration Modeling by Partial Least-Squares and Principal Component Regression and its Optimization Using an Improved Leverage Correction for Prediction Testing", *Chemometrics and Intelligent Laboratory Systems*, 9 (1990) 45-63.

Jansson, P., "Neural Networks: An Overview", *Analytical Chemistry*, vol. 63, No. 6, Mar. 15, 1991, pp. 357-362.

Donahoe, T. M., et al., "A New Noninvasive Backscattering Oximeter", *IEEE/Seventh Annual Conference of the Engineering in Medicine and Biology Society*, pp. 144-147, 1985.

\* cited by examiner

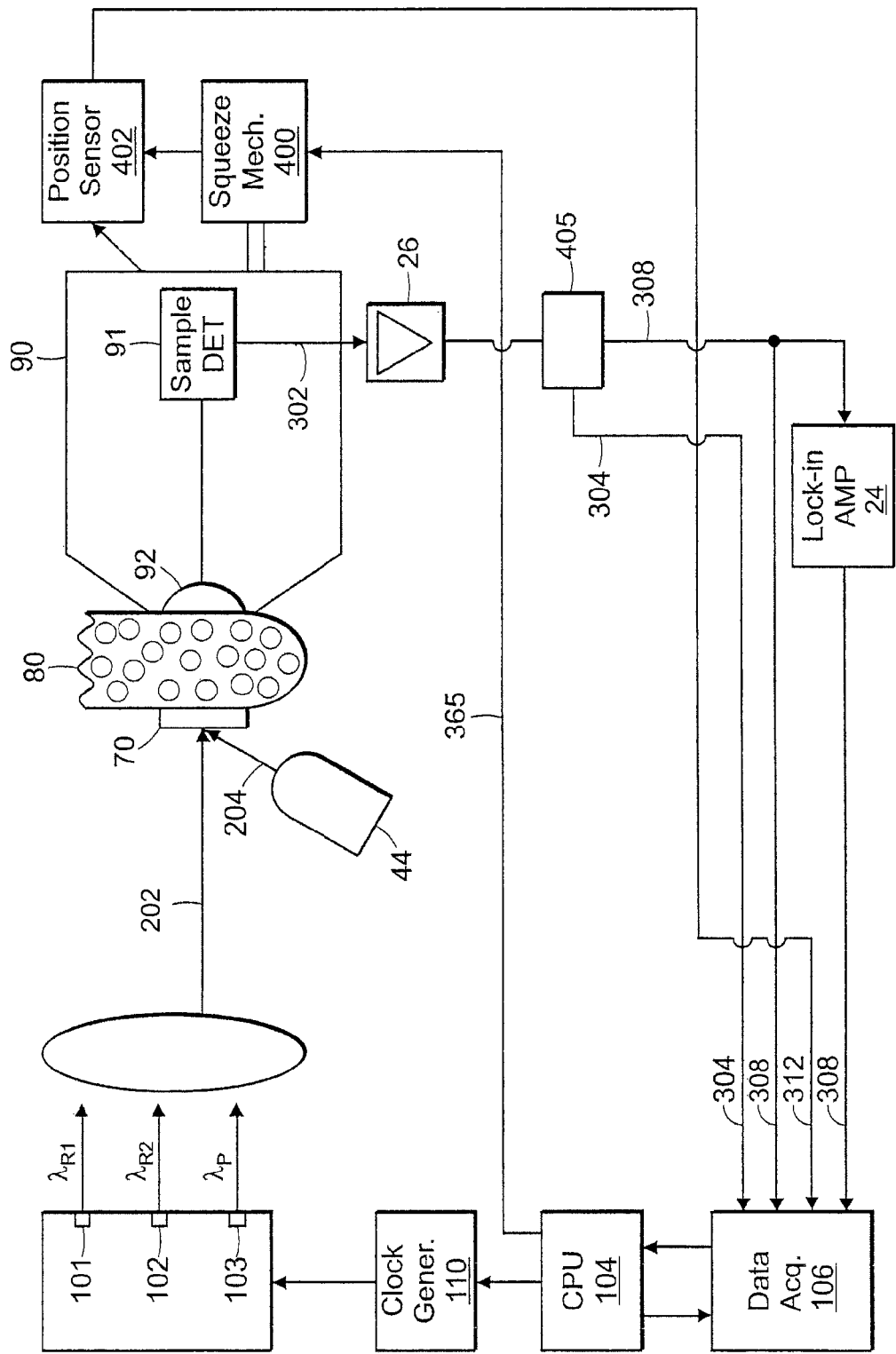

THREE DIODE OPTICAL BRIDGE SYSTEM

RELATED APPLICATIONS

This is a continuation-in-part of U.S. application Ser. No. 11/335,833, filed Jan. 19, 2006 now abandonded, which is a continuation of U.S. application Ser. No. 10/134,310, filed Apr. 26, 2002, now U.S. Pat. No. 7,003,337, issued Feb. 21, 2006. The entire teachings of the above applications are incorporated herein by reference.

BACKGROUND OF THE INVENTION

This invention relates to the non-invasive measurement of the concentration of substances that absorb electromagnetic radiation, such as light or infrared radiation, in absorbing and turbid matrices, such as human or animal body tissue, using a probe beam of electromagnetic radiation. The invention is particularly applicable to glucose measurement in human tissue using near-infrared radiation. It is, however, generally applicable to measurements of the concentration of any species that absorbs electromagnetic radiation, especially in strongly absorbing and turbid matrices.

The present invention is an improvement over U.S. Pat. No. 5,099,123, issued to Harjunmaa (hereafter, the "'123 patent"), which is incorporated herein in its entirety by reference. The balanced differential (or "optical bridge") method disclosed in the '123 patent utilizes two wavelengths for target analyte concentration measurements. The first, or principal wavelength is chosen such to be highly absorbed in the target analyte. The second, or reference wavelength is chosen using a balancing process so that both wavelengths have substantially identical extinction coefficients in the background matrix. A radiation beam is generated that contains these two wavelengths in alternate succession at a suitable frequency. When the beam is properly balanced for the measurement, a sample detector, placed to measure radiation transmitted or reflected by the sample matrix that contains only a residual amount of the target analyte, will detect only a very small alternating component in the radiation, regardless of the thickness of the sample. When there is a relatively substantial amount of the target analyte in the sample matrix, however, the detector will detect a significant alternating signal synchronous with the wavelength alternation. This alternating signal is amplified and is then detected using a phase-sensitive detector (or lock-in amplifier). The optical bridge balancing process entails nulling out the alternating signal from the sample detector by systematically varying the relative intensities and/or wavelengths of the repetitive radiation periods.

Subsequently in U.S. Pat. No. 5,178,142, (hereafter, the "'142 patent"), which is also incorporated by reference herein in its entirety, Harjunmaa et al. disclosed an improved method and apparatus in which the concentration measurement is performed using a two-wavelength alternating radiation probe beam which interacts with the tissue. One of the wavelengths is used as a reference wavelength, and the other is the principal wavelength. The reference wavelength is tunable to account for the expected variability of the background spectrum. After passing through the matrix that contains a given reference concentration of analyte, detected signals from the probe beam are balanced or nulled by controlling the reference wavelength and the intensity relations of the two wavelengths. Next, the blood content of the sample is changed. The alternating component of the interacted probe beam is then detected. The amplitude of the alternating component of the signal given by the sample detector is proportional to the concentration of analyte or the difference from a preset reference analyte concentration.

Other related patents include U.S. Pat. Nos. 5,112,124; 5,137,023; 5,183,042; 5,277,181 and 5,372,135, each of which is incorporated by reference herein in its entirety.

SUMMARY OF THE INVENTION

This invention relates to systems and methods for generating a beam of electromagnetic radiation for non-invasively estimating the concentration of a target analyte in a sample.

The present invention relates to an improvement to the known balanced differential, or "optical bridge," systems for measuring the concentration of a target analyte in a sample. As used herein, "optical bridge" refers to an apparatus and/or method for quasi-simultaneous differential optical measurement of very small absorbance differences of a sample, performed at one or more wavelength pairs. According to one aspect, the improved optical bridge method and system of present invention includes: 1) time-series measurements during and after a sample thickness variation; 2) synchronization of the measurements with the unbound fluid (e.g. blood) inrush into the sample; and, 3) the use of parameters extracted from the time-series measurements to compensate for daily and long-term variations in the absorption of the sample background matrix. An advantage of the present invention is the ability to generate the required combined beam without a wavelength-tunable light source. Accordingly, a simpler measurement system is provided which is capable of improved accuracy of target analyte concentration estimation.

An apparatus according to this invention includes a source for producing a beam of electromagnetic radiation. This beam consists of time multiplexed components (principal and reference) of desired narrow line-width wavelengths, and is produced, for instance, using three or more diode lasers.

During a measurement, the alternating-wavelength probe beam passes through (or is reflected from) a sample mounted in a compression device. The compression device controllably varies the thickness of the sample (and consequently its unbound fluid content) during the measurement. A sample detector is positioned to receive the probe beam after it passes through the sample. The sample detector then feeds a signal to an analog signal pre-processing module that includes the hardware implementation of the optical bridge. The output optical bridge signal is then fed to a processor, which is programmed to calculate the target analyte concentration in the unbound fluid, based on parameters extracted from the sample detector signal and other auxiliary variables and time-varying signals.

Another advantage is that the detailed spectral structure of the combined optical system and sample in the region of the reference wavelength has no effect on the balancing process.

One of the auxiliary signals used in the calculation of the target analyte concentration is a time-varying estimate of the unbound fluid (e.g. blood) content within the sample. This estimate can be obtained, for example, by a separate, auxiliary blood signal detector measuring the sample transmission (or reflection) of light from a separate light source that provides radiation distinct from the wavelengths used for the target analyte measurement, preferably at a wavelength where hemoglobin absorbs, and even more particularly at a wavelength where hemoglobin absorption is independent of its oxidation state (i.e., isosbestic point). In other embodiments, a laser Doppler flow meter may be used to obtain a measurement of sample blood content.

A method, according to this invention, for non-invasively measuring a concentration of a target substance (e.g., glucose) in a matrix (e.g., tissue) includes the following steps. First, the sample is compressed by the compression device to force out the unbound fluid that contains the majority of the target analyte. The sample is then illuminated with the probe beam of electromagnetic radiation. Preferably, the beam includes a principal period and a reference period, wherein during the principal period the effective wavelength of the radiation is more strongly absorbed by a target analyte, such as glucose, than is the effective wavelength of the radiation during the reference period. By way of illustration, the wavelength that is strongly absorbed by glucose can be between approximately 1550 and 1700 nm, and the wavelength lightly absorbed by glucose can be between approximately 1350 and 1430 nm.

In one embodiment, the principal wavelength is universally pre-set, or pre-set individually for each patient. In this embodiment, the reference radiation consists of a mixture of two separate wavelengths that, when mixed at the entry to the sample volume, has an effective wavelength that is a function of the relative intensities of the two component radiations. More precisely, the effective wavelength $\lambda_R$ is $$\lambda_R = (I_{R1} \cdot \lambda_{R1} + I_{R2} \cdot \lambda_{R2})/(I_{R1} + I_{R2})$$

where $I_{Ri}$=intensity at wavelength $\lambda_{Ri}$

The intensity relation is adjusted during a balancing process. This balancing process is performed prior to measurement. The balancing process comprises, for example, adjusting the intensity of one of the alternating radiation periods, while maintaining the sum of the two component intensities constant, in order to obtain a substantially-zero alternating component of the sample detector signal (i.e. the optical bridge signal) at chosen sample thicknesses/pressures exerted by the sample compression device. In this embodiment, two fixed lasers can replace one tunable laser, which is typically a more expensive laser. The optical bridge is "balanced" when there is substantially no alternating component in the signal generated by the sample detector. A properly balanced optical bridge means that the principal and effective reference wavelengths are equally absorbed by the sample matrix, which contains only residual amounts of the target analyte.

A measurement sequence comprises a series of individual measurements of intensities of the transmitted/reflected probe beam wavelength components obtained by the sample and auxiliary detector(s). This series of measurements is obtained during an alteration of sample thickness, and also over the subsequent sample content equilibration process that follows the alteration of sample thickness. The measurements are preferably obtained while the unbound fluid content of the sample is changing.

In a preferred embodiment of the invention, the sample thickness change is synchronized with the heartbeat. One advantage of this is that since the influx speed of blood depends on the blood pressure, performing the uncompression at a constant phase of the cardiac cycle produces blood refill time profiles that are substantially constant in shape. The cardiac phase can be chosen so as to also provide the largest possible blood content change.

Measurements of auxiliary parameters (including, for example, unbound fluid content, temperature of sample and detector, sample thickness, and/or electronic control system operational parameters) accompany the measurements of the probe beam intensities. The recorded data is further combined with corresponding estimates of the time-varying unbound fluid content over the same time. An algorithm, based on modeling, is used to extract characteristic parameters from the time-series profiles, and combines these parameters with other measured parameters to achieve improved specificity and sensitivity in the estimation of the target substance concentration.

Using the method of the present invention, the accuracy of the target analyte measurement is improved by isolating and quantifying the component of the optical bridge signal that results from the presence of the analyte rather than other "parasitic" factors. More specifically, where the targeted analyte is located primarily within the unbound fluid rather than the fixed structure of the matrix, the magnitude of the optical bridge signal depends directly on the amount of fluid within the sample. Thus, if the varying unbound fluid content of the sample is estimated and plotted against the magnitude of the optical bridge signal over time, the result is a substantially straight line whose slope is directly related to the concentration of analyte in the sample, assuming that the other factors contributing to the "parasitic" signal, including shifts in the effective wavelength due to changes in sample thickness, remain relatively constant during the measurement process.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 1 is a schematic of a system for non-invasive measurement of a target analyte having a three-diode optical bridge apparatus.

DETAILED DESCRIPTION OF THE INVENTION

A description of example embodiments of the invention follows.

The features and other details of the method of the invention will now be more particularly described with reference to the accompanying drawings and pointed out in the claims. It will be understood that the particular embodiments of the invention are shown by way of illustration and not as limitations of the invention. The principal features of this invention can be employed in various embodiments without departing from the scope of the invention.

Exemplary embodiments of an optical bridge system are shown and described in commonly-owned U.S. application Ser. No. 11/335,833 and U.S. Pat. No. 7,003,337, the entire teachings of which are incorporated herein by reference. One embodiment of an optical bridge apparatus for measuring glucose concentration in blood based on transmitted light through the is shown in FIG. 1. A similar apparatus may be designed which uses reflected or back-scattered light instead of transmitted light.

In the preferred embodiment, three fixed-wavelength monochromatic light sources 101, 102, 103, such as laser diodes, may be used to produce the probe beam 202.

Clock generator 110 produces a timing signal at the desired chopping frequency $f_{ch}$ needed for time multiplexing of the principal and reference components, as well as the blood-estimation component, of the probe beam. The CPU 104 generates signals for controlling the principal intensity $I_P$, both wavelengths $\lambda_P$ and $\lambda_R$, and the chopping frequency $f_{ch}$ of the probe beam 202.

The probe beam is directed onto diffuser plate 70. Placing a diffuser plate in the beam path before the sample provides the advantage of minimizing the effects of the variation in the scattering properties of the sample. The preferred diffuser plate is of the holographic type that has substantially constant diffusing properties across the pertinent wavelength range. The sample specimen 80, such as an earlobe, lip, cheek, nasal septum, tongue, or the skin between the fingers or toes of the subject, is placed between diffuser plate 70 and sample detector lens 92, and is compressed by moving the measurement head 90, mounted on compression mechanism 400. The probe beam 202 transmitted through sample 80 is focused by sample detector lens 92, and directed to sample detector 91. The sample detector 91 detects the intensity at each of the wavelength periods of the probe beam 202 transmitted through sample 80, and sends an electrical signal 302 to preamplifier 26 and on to a demultiplexer 405 that separates the blood estimation wavelength signal from the balanced-pair signal; the latter is fed to a phase sensitive detector (or lock-in amplifier) 24. The output signal 308 from the phase sensitive detector 24 is proportional to the difference (or ratio) of the principal and reference intensities detected by sample detector 91. This signal 308 is referred to as the optical bridge signal.

In this embodiment, a separate auxiliary radiation source such as an infrared or visible-light LED 44, is used to provide an estimate of the sample blood content. This auxiliary radiation source 44 produces a blood detection beam 204 that is directed onto the diffuser plate 70 and into the sample. An LED operating at a wavelength of, for instance 525 nm (an isosbestic wavelength for hemoglobin), provides a good sensitivity to blood. When the balanced-pair and blood detection wavelengths are properly time-multiplexed, the sample detector 91 can be used to detect the transmitted portion of the blood detection beam 204, producing a blood signal 304.

Other possible techniques for obtaining an estimate of the blood content include ultrasound and electrical impedance plethysmography.

To perform a measurement, the sample 80 is introduced between diffuser plate 70 and sample detector lens 92. The measurement head 90 is moved by compression mechanism 400 to gently compress sample 80 until a predetermined pressure is exerted on sample 80. The preferred embodiment of compression mechanism 400 includes a miniature linear actuator. Its step size, speed and travel distance are controlled by the CPU 104. Although this embodiment uses an electrical actuator, a hydraulic or a pneumatic actuator could also be used, with the ensuing advantages of compactness of the compression mechanism.

In this description, three different types of probe beam attenuations are distinguished. First is the background matrix, the second is the target analyte, while the third is the unbound fluid attenuation.

The background matrix attenuation results from the absorption of probe beam 202 by sample constituents whose concentrations are substantially constant throughout fixed sample compartments. The target analyte attenuation is caused by absorption of probe beam 202 by the target analyte (e.g. glucose), which is mostly concentrated in the unbound fluid (e.g. blood). When the tissue is sufficiently compressed, the unbound fluid, along with the target analyte (e.g. glucose), is substantially displaced from the sample 80. Since the concentration of the target analyte in the unbound fluid is different than its concentration in the background matrix (e.g. intracellular concentration), its average concentration in the beam path changes as a result of the compression. This concentration change allows the target analyte to be detected by this method.

The principal wavelength $\lambda_P$ of probe beam 202 is selected in such a way to have high attenuation by the target analyte. The principal wavelength intensity $I_P$ is set to achieve an optimal transmitted signal intensity. The effective reference wavelength $\lambda_R$ of the probe beam is selected during the optical bridge balancing process. Its intensity $I_R$ should be adjusted before each measurement as explained below in the description of the measurement process.

In the following text, a simple to understand example of a bridge balancing process is presented. It will be readily understood by those skilled in the art that different, more complex, bridge balancing procedures can also be used, with corresponding variations of the signal processing algorithm.

In the first step of bridge balancing, sample 80 is sufficiently compressed to remove the major amount of unbound fluid from the sample tissue. The principal wavelength parameters $\lambda_P$ and $I_P$ are set, and the effective reference wavelength $\lambda_R$ is initialized. The probe beam 202 is directed at the sample, and the optical bridge is balanced or nulled by adjusting the intensity of the probe beam reference wavelength intensity $I_R=I_{R1}+I_{R2}$ to obtain a substantially-zero optical bridge signal 308. In other embodiments, the reference wavelength intensity $I_R$ is set, while the principal wavelength intensity $I_P$ is adjusted to balance the bridge. Next, the sample compression pressure is released by a predetermined amount (typically less than 0.1 mm) and the probe beam effective reference wavelength $\lambda_R$ is adjusted by controlling the intensity ratio of $\lambda_{R1}$ and $\lambda_{R2}$ using a signal from CPU 104 so as to again achieve a substantially-zero optical bridge signal 308. The initial compression pressure is chosen such that, even after releasing sample 80 by several times the incremental thickness, there is nearly no unbound fluid reflow into the sample. Changes in the optical bridge signal 308, due to this thickness increase result merely from increased background matrix thickness and not from any substantial influx of fluid. Sample 80 is then uncompressed again by one step thickness, and the intensity at the reference (or principal) wavelength is again adjusted by the CPU 104 to achieve minimum optical bridge signal.

This stepwise increasing thickness procedure may be continued until a substantially-zero optical bridge signal is obtained. Once the sample thickness has been increased, the procedure may also be reversed, using stepwise decreasing thicknesses. When this balancing procedure is completed, the absorption coefficient of sample 80 in its compressed state is substantially equal at the two wavelengths $\lambda_P$ and effective $\lambda_R$.

In one embodiment, the balancing is limited to only one cycle in order to speed up the measurement and reduce the compression stress on the sample.

This completes the optical bridge balancing phase; at this point both wavelengths and their intensities have been established. The instrument is ready to perform a measurement. A typical sequence for measurement of glucose in blood will be described in the following text, with reference to the measurement apparatus of the FIGURE.

Generally, the sample 80 is maintained in the compressed state to displace the unbound fluid content for a time period of approximately 1 to 100 seconds.

Next, continuous measurements of the time-varying signals begin, including time-varying measurements of the optical bridge output 308, blood signal 304, and position sensor 402 output 312.

Once these measurements begin, the compression mechanism 400 then starts opening the measurement head 90 by an amount and rate set by the CPU 104. The amount of head opening may be fixed (e.g. 0.5 mm for a human ear), or may be thickness dependent (e.g. 20% of the compressed sample thickness). It is directly controlled from the subroutine for compression control, via connection 365. The purpose for the fast opening phase is to allow the unbound fluid that contains the target analyte to return into the sample.

The opening of the compression mechanism causes a change in the sample composition, which makes the sample absorb differently at the principal wavelength and the effective reference wavelength. This relative change in absorption results in a non-zero optical bridge signal 308. The measurements continue until stopped by CPU 104. Typically, the time-varying signal series should contain several hundred data sets, which are recorded, in a data acquisition block 106, over a measurement time period of approximately 0.1 to 10 seconds after the sample uncompression begins.

This concludes the measurement process, which is then followed by signal processing.

Having thus described a few particular embodiments of the invention, various alterations, modifications and improvements will readily occur to those skilled in the art. Such alterations, modifications and improvements as are made obvious by this disclosure are intended to be part of this description though not expressly stated herein, and are intended to be within the spirit and scope of the invention.

For example, while the method is here described as applied to an optical bridge employing non-tunable lasers, it can also be applied to different implementations of the optical bridge, such as one equipped with light emitting diodes or superluminescent light emitting diodes or other means to generate a beam containing the required wavelength combinations. Moreover, although the method is here described with a focus toward measuring the concentration of glucose in blood, the method and apparatus of this invention may also be employed to detect the concentration of other analytes such as cholesterol, urea, heavy metals, alcohol, nicotine or drugs in blood or other fluids. Further, sinusoidal, rather than square, modulation waveforms that are set 180° out of phase and result in a substantially constant total intensity, can alternatively be used to form the combined radiation beam. Also, measurements of radiation reflected or back-scattered by the tissue, rather than transmitted radiation, can be performed to obtain the desired data.

Accordingly, the foregoing description is by way of example only, and not limiting. The invention is limited only as defined in the following claims and equivalents thereto.

While this invention has been particularly shown and described with references to example embodiments thereof, it will be understood by those skilled in the art that various changes in form and details may be made therein without departing from the scope of the invention encompassed by the appended claims.

What is claimed is:

1. A method of generating a beam of electromagnetic radiation for the non-invasive measurement of a concentration of a target analyte in a fluid within a sample matrix, the method comprising: directing a combined beam of electromagnetic radiation at the sample, the combined beam including at least two repetitive periods of radiation including a principal beam and a reference beam, the principal and reference beams having different wavelengths, the target analyte having different absorption coefficients for the different wavelengths, and the reference beam including a mixture of at least two radiations of different wavelengths, having an effective wavelength equal to an intensity-weighted mean of the two component wavelengths, wherein intensities of the periods of radiation are adjusted when the sample is at a first sample fluid state, and at least one effective wavelength of the at least two repetitive periods of radiation is selected to minimize detectable transmission or reflection difference when the sample is at a state different from the first state.

2. The method according to claim 1, wherein the sample matrix comprises biologic tissue and the fluid comprises blood.

3. The method of claim 1, wherein a wavelength strongly absorbed by glucose is substantially in the range of 1550 to 1700 nm, and a wavelength lightly absorbed by glucose is substantially in the range of 1350 to 1430 nm.

4. The method of claim 1, further including producing the combined beam by three or more diode lasers.

5. A system for the non-invasive measurement of a concentration of a target analyte in a fluid within a sample matrix, comprising: a source of electromagnetic radiation that is configured to direct a combined beam of electromagnetic radiation at the sample matrix, the combined beam including at least two repetitive periods of radiation including a principal beam and a reference beam, the principal and reference beams having different wavelengths, the target analyte having different absorption coefficients for the different wavelengths, the reference beam including a mixture of at least two radiations of different wavelengths having an effective wavelength equal to the intensity-weighted mean of the two component wavelengths, a sample detector that detects the concentration of the target analyte by measuring radiation reflected to absorbed by the sample matrix, and a controller configured to adjust intensities of the periods of radiation when the sample is at a first sample fluid state, and at least one effective wavelength of the at least two repetitive periods of radiation is selected to minimize detectable transmission or reflection difference when the sample is at a state different from the first state.

6. The system of claim 5, wherein the source of electromagnetic radiation comprises three or more laser diodes.

* * * * *